(12) United States Patent
Winkelman

(10) Patent No.: US 10,010,274 B2
(45) Date of Patent: Jul. 3, 2018

(54) SYSTEMS, DEVICES AND METHODS FOR IN SITU CALIBRATION OF IMPLANTABLE SENSORS

(71) Applicant: James Winkelman, Chestun Hill, MA (US)

(72) Inventor: James Winkelman, Chestun Hill, MA (US)

( * ) Notice: Subject to any disclaimer, the term of this patent is extended or adjusted under 35 U.S.C. 154(b) by 0 days.

(21) Appl. No.: 14/365,172

(22) PCT Filed: Dec. 17, 2012

(86) PCT No.: PCT/US2012/070025
§ 371 (c)(1),
(2) Date: Jun. 13, 2014

(87) PCT Pub. No.: WO2013/090882
PCT Pub. Date: Jun. 20, 2013

(65) Prior Publication Data
US 2014/0371553 A1    Dec. 18, 2014

Related U.S. Application Data

(60) Provisional application No. 61/576,934, filed on Dec. 16, 2011.

(51) Int. Cl.
*A61B 5/1455* (2006.01)
*A61B 5/145* (2006.01)
(Continued)

(52) U.S. Cl.
CPC ........ *A61B 5/14532* (2013.01); *A61B 5/1455* (2013.01); *A61B 5/1473* (2013.01);
(Continued)

(58) Field of Classification Search
None
See application file for complete search history.

(56) References Cited

U.S. PATENT DOCUMENTS 6,254,586 B1    7/2001  Mann et al.
2008/0119707 A1*  5/2008  Stafford ............. A61B 5/14503
                                                        600/365

(Continued)

OTHER PUBLICATIONS

PCT International Search Report and Written Opinion, PCT/US2012/070025, dated Feb. 26, 2013 (14 pages).

*Primary Examiner* — Eric Winakur
*Assistant Examiner* — Marjan Fardanesh
(74) *Attorney, Agent, or Firm* — Thomas J. Engellenner; Reza Mollaaghababa; Pepper Hamilton LLP

(57) ABSTRACT

The systems, methods, and devices described herein generally involve monitoring and/or quantification of various analyte levels in a biological fluid using one or more implantable sensors. In various aspects, systems, methods, and devices described herein can provide for the in situ calibration and/or cleaning of such sensors when implanted in the patient. The systems and devices disclosed herein can, for example, continuously or serially measure analytes within a biological fluid in vivo (e.g., without extracting the biological fluid from the patient) and periodically calibrate and/or clean the sensor without using finger sticks or additional, invasive calibration techniques. By way of non-limiting example, systems and devices disclosed herein can enable continuous monitoring of analyte concentrations (e.g., glucose) in subcutaneous interstitial fluid for several hours to a few days.

14 Claims, 5 Drawing Sheets

(51) Int. Cl.
*A61B 5/1495* (2006.01)
*A61B 5/1473* (2006.01)

(52) U.S. Cl.
CPC ........ *A61B 5/1495* (2013.01); *A61B 5/14503* (2013.01); *A61B 2560/0228* (2013.01)

(56) References Cited

U.S. PATENT DOCUMENTS

| | | |
|---|---|---|
| 2008/0234562 A1 | 9/2008 | Jina |
| 2009/0069650 A1* | 3/2009 | Jennewine ........ A61M 5/14248 600/309 |
| 2009/0131860 A1* | 5/2009 | Nielsen ............. A61M 5/14248 604/66 |
| 2010/0213079 A1 | 8/2010 | Willis |
| 2010/0298684 A1 | 11/2010 | Leach et al. |
| 2010/0324853 A1 | 12/2010 | Wang et al. |

* cited by examiner

SYSTEMS, DEVICES AND METHODS FOR IN SITU CALIBRATION OF IMPLANTABLE SENSORS

CROSS-REFERENCE TO RELATED APPLICATIONS

This application claims the benefit of priority of U.S. Provisional Application No. 61/576,934, filed Dec. 16, 2011, and entitled "In-Situ Calibration Systems for Implantable Glucose Sensors," which is incorporated herein in its entirety.

FIELD

The present teachings relate to the field of analyte monitoring within a biological fluid. In various aspects, systems, devices, and methods are provided for the monitoring and/or quantification of various analyte levels using one or more implantable sensors, and for the in situ calibration of such sensors. Exemplary applications include but are not limited to continuous glucose monitoring.

BACKGROUND

Clinical chemistry enables the analysis of biological fluids for diagnosing, monitoring, and/or treating the medical condition of a patient. By way of example, determining the level of analytes such as glucose, lactate, creatinine, electrolytes, and oxygen can be vitally important for monitoring and/or maintaining a patient's health and treatment. Moreover, a patient's reaction to the administration of certain substances (e.g., glucose) can be used in diagnostic stress-tests. Similarly, by monitoring the level of xenobiotics such as insulin or drugs and their metabolites, physicians can diagnose kidney and liver disorders or select appropriate dosing in drug treatment. For example, monitoring the pharmacokinetics of a drug under treatment conditions in a particular patient can allow individualized optimization of the treatment schedule and help avoid potentially serious drug-drug interactions.

Though centralized clinical laboratories can provide a wide array of assays for accurately determining the presence and/or concentration of various analytes, clinical laboratories typically require that a sample (e.g., blood) be obtained from a patient, shipped to a laboratory, and processed and tested prior to the results being communicated back to the patient's physician. While recent advances in point-of-care (POC) diagnostics have enabled some laboratory tests to be quickly performed at the patient's bedside, these assays are not without drawbacks as the accuracy and precision of POC instruments often suffer relative to their central lab counterparts.

By way of example, blood glucose has been the most frequently performed clinical chemistry laboratory test for the past several decades based, in part, on it serving as the primary indication for diabetes detection and monitoring of therapy. Over the last 15 years, however, self-testing of blood glucose has become increasingly common with the advent of POC glucometers that allow an individual to lance their fingertip, expel a drop of blood onto a test strip that can be inserted into the glucometer, and obtain an almost immediate measurement of his or her blood glucose level. Though POC glucometers and strips need only meet a +/−15% c.v. for approval by the FDA (clinical laboratory tests for glucose are remarkably accurate and precise with typical c.v.s of +/−2.0%), the advantages associated with frequent self-testing are believed to outweigh the relative lack of accuracy such that self-testing provides the basis for the current standard of care for diabetes. It has been shown, for example, that frequent blood glucose testing leads to a reduction in cardiovascular, renal, ophthalmological, and other morbidities associated with diabetes. Indeed, data generated as a result of the availability of frequent, instantaneous blood glucose measurements has prompted many in the medical community to promote tight glycemic control for diabetics and non-diabetic patients alike.

Despite the frequency of sampling (e.g., at 15-, 30-, 60-, or 240-minute intervals as specified by protocols), monitoring provided by glucometers and other analyte monitors is nonetheless discontinuous, providing a snapshot of analyte levels in the blood at the moment that the sample was obtained. Accordingly, systems have been developed to continuously measure the concentration of analytes in subcutaneous interstitial fluid, for example, since the concentration of certain analytes (e.g., glucose) is highly correlated between these two fluid compartments (Bantle, et al., J Lab Clin Med 1997; 130: 436-441). By way of example, sensors for continuous monitoring of certain analytes (e.g., glucose) in interstitial fluid are known in the art. U.S. Pat. No. 6,579,690 of Bonnecaze et al. and U.S. Application Pub. No. 2008/0027296 of Hadvary et al., which are incorporated herein by reference, provide continuous analyte monitoring systems that may enable better glycemic control through continuous, real-time monitoring of a patient's interstitial fluid glucose levels. Some such systems, for example, employ an electrochemical sensor that can be implanted within subcutaneous tissue and remain in contact with the interstitial fluid for an extended time (e.g., several hours to a week or more). The voltage output of the sensor can be transmitted to a data processing unit for converting the sensor output to a blood glucose equivalent value.

Like POC glucometers and other POC analyte measurement systems, implantable analyte monitoring systems can suffer from diminished accuracy and precision relative to their clinical laboratory counterparts. Moreover, the long-term implantation of these monitors can diminish the reliability of the data transmitted by the sensor(s) as other components in body fluids (e.g., proteins) can contaminate the sensors and cause inaccurate readings. As a result, current continuous analyte monitoring systems generally require frequent calibration or confirmation using other more invasive and/or less convenient techniques. By way of example, prior to treating a patient in whom their continuous blood glucose monitor indicates a low blood glucose level, a medical caretaker is generally required to confirm the levels using the standard-of-care POC glucometers. Likewise, diabetics using implantable, continuous glucose monitors are nonetheless prompted to provide a finger stick measurement for regular calibration of their monitors and/or prior to treatment.

Accordingly, there remains a need for improved accuracy and reliability of implantable, continuous analyte monitoring systems.

SUMMARY

The systems, methods, and devices described herein generally involve monitoring and/or quantification of various analyte levels in a biological fluid using one or more implantable sensors. In various aspects, systems, methods, and devices described herein can provide for the in situ calibration and/or cleaning of such sensors when implanted in the patient. The systems and devices disclosed herein can, for example, continuously or serially measure analytes within a biological fluid in vivo (e.g., without extracting the biological fluid from the patient) and periodically calibrate and/or clean the sensor without using finger sticks or additional, invasive calibration techniques. By way of non-limiting example, systems and devices disclosed herein can enable continuous monitoring of analyte concentrations (e.g., glucose) in subcutaneous interstitial fluid for several hours to a few days.

In one aspect, a system for monitoring the concentration of an analyte is provided. The system can include a sensor configured to be implanted at an implant site in a patient's skin, the sensor configured to sense an analyte present in a biological fluid at the implant site. The system can additionally include a reservoir, which contains a calibration fluid having a known concentration of the analyte, and a conduit for delivering the calibration fluid from the reservoir to the implant site.

Various analytes in a variety of biological materials can be sensed. By way of non-limiting example, the biological fluid can be interstitial fluid (e.g., subcutaneous interstitial fluid), intravascular fluid (e.g., venous or arterial blood and portions thereof such as serum), and urine. Moreover, the sensed analyte(s) can be one or more of glucose, lactate, creatinine, oxygen, alcohol, urea, electrolytes (e.g., potassium, calcium, magnesium, manganese, bicarbonate, and sodium) and drugs. In one exemplary aspect, the system can sense the concentration of glucose in subcutaneous interstitial fluid.

Sensors for use in the system can have a variety of configurations. For example, the sensor can be an electrochemical or optical sensor. In some aspects, the sensor can extend to a depth below the skin surface from a housing configured to be disposed on the skin surface. The sensor, for example, can comprise a microneedle extending from the housing, the microneedle being configured to pierce the skin. In some aspects, the microneedle can have one or more sensing sites. In some aspects, the sensor housing can additionally contain additional modules. By way of example, the housing can contain one or more of a data processing unit and a transmitting unit. In some embodiments, the reservoir can be contained within said housing. A pump, for example, can also be contained within the housing for pumping the calibration fluid through the conduit. In certain aspects, the system can also include a controller for controlling the pump so as to deliver a predetermined amount of the calibration fluid to the implant site. By way of example, the controller can be configured to control the pump to deliver the predetermined amount of the calibration fluid to the implant site a predetermined number of times with a predetermined time interval. In some aspects, the controller can control a number of repetitions of calibration fluid delivery, an amount of the calibration fluid delivered, and a time interval between each delivery. By way of non-limiting example, the number of repetitions of calibration fluid delivery can be 1 to 5, the amount of the calibration fluid delivered can be from about 2 to about 50 microliters for each delivery, and the time interval between each delivery can be from about 1 minute to about 24 hours.

In some aspects, the conduit and sensor can extend from the housing adjacent to one another. In other aspects, the sensor can extend through a fluid pathway defined by the calibration fluid delivery conduit. For example, the conduit can be a cannula or sheath extending from the housing and surrounding the sensor and through which the calibration solution can be delivered to the implant site in a fluid pathway between the sheath and the sensor. In some aspects, the sheath can enclose a distal end of the sensor such that the calibration solution can be delivered to the implant site therearound.

In some aspects, the sensor can have one or more sensing sites. In some embodiments, the outlet of the conduit can be disposed relative to the one or more sensing sites such that fluid delivered by the conduit to the implant site is directed at the one or more sensing sites. In some aspects, the fluid delivered by the conduit can be configured to remove contaminants from the sensing sites.

Methods for operating an implantable monitoring system are also provided herein. In some aspects, the methods include delivering a calibration fluid of a known concentration to a sensor implanted at an implant site of a patient, the sensor being configured to sense a parameter at the implant site. The method can further include determining a calibration value following delivery of the calibration fluid to the implant site. Exemplary parameters include, for example, the concentration of an analyte present at the implant site. As will be discussed in detail below, various parameters can be sensed. By way of example, the concentration of one or more analyte(s) such as glucose, lactate, creatinine, oxygen, alcohol, urea, electrolytes (e.g., potassium, calcium, magnesium, manganese, bicarbonate, and sodium) and drugs can be sensed.

In one exemplary aspect, the concentration of glucose in subcutaneous interstitial fluid can be sensed.

In some aspects, methods provided herein can further include measuring a value of the parameter at the implant site in the absence of the calibration fluid. In a related aspect, the measured value of the parameter can be adjusted based on the calibration value to determine a calibration-corrected value of the parameter. In various embodiments, the calibration value can be used to adjust measured values obtained prior to or subsequent to determining the calibration value. In some embodiments, the calibration-corrected value of the parameter can be outputted (e.g., to the patient or a caretaker). In various aspects, the measured value of the parameter can be determined substantially continuously.

In some aspects, the steps of delivering the calibration fluid and determining the calibration value can be repeated prior to measuring the value of the parameter in the absence of calibration fluid if said calibration value is not within a specified percentage of an expected value.

In various aspects, the steps of delivering the calibration fluid and determining the calibration value can be repeated after a predetermined time interval. By way of non-limiting example, the predetermined time interval can be from about 1 minute to about 24 hours. In some aspects, each iteration of delivering the calibration fluid can comprise delivering from about 2 to about 50 microliters of calibration fluid to the implant site.

The calibration value can be determined in a variety of ways. By way of example, determining the calibration value comprises measuring a value of the parameter following delivery of the calibration fluid and comparing said measured value of the parameter with the known concentration of the calibration fluid. In some aspects, for example, determining the calibration value can comprise dividing a measured value of the parameter following delivery of the calibration fluid by the known concentration of the calibration fluid. In various embodiments, determining the calibration value can comprise measuring a change in a value of the parameter following delivery of the calibration fluid over time and comparing the measured change in value of the parameter over time with an expected change in the value of the parameter over time in response to the delivery of the known concentration of the calibration fluid.

The sensor can have a variety of configurations. For example, the sensor can extend from a sensor housing that is disposed on a patient's skin surface and that includes a data processing unit for determining the calibration-corrected value. In some embodiments, the sensor can have a tip configured to pierce the patient's skin. The sensor can sense a parameter at the implant site using a variety of modalities. By way of example, the sensor can be one of an electrochemical and optical sensor.

In some aspects, delivering the calibration fluid of known concentration can comprise pumping the calibration fluid from a reservoir contained with a sensor housing disposed on the patient's skin and from which the sensor extends. In various embodiments, the methods can also include delivering the calibration fluid to the sensor to remove contaminants from a surface thereof.

These and other embodiments, features, and advantages will become apparent to those skilled in the art when taken with reference to the following more detailed description of various exemplary embodiments in conjunction with the accompanying drawings.

DETAILED DESCRIPTION

The following detailed description should be read with reference to the drawings. The drawings, which are not necessarily to scale, depict selected embodiments and are not intended to limit the scope of the invention. The detailed description illustrates by way of example, and is not intended to limit the scope of the invention.

The teachings herein generally provide systems, devices, and methods for monitoring and/or quantification of various analyte levels using one or more implantable sensors, and for the in situ calibration of such sensors. By way of example, the present teachings can enable continuous and/or serial measurements over an extended period of time of one or more analytes within a biological fluid using an implantable sensor. In various aspects, the implantable sensors can be periodically calibrated in situ, without extraction of biological fluid from the patient and removal of the sensor itself. By way of non-limiting example, systems and devices disclosed herein can enable continuous monitoring of analyte concentrations (e.g., glucose) in subcutaneous interstitial fluid for several hours to a few days. Though particular features of exemplary analyte monitoring systems and sensors are described, it will be appreciated by the person skilled in the art that the calibration devices and methods described herein can be used in conjunction with any known or hereafter developed implantable analyte monitoring systems and sensors, modified in accordance with the present teachings.

The implantable analyte monitoring systems can have a variety of configurations but generally include a sensing module at least a portion of which can be implanted in a patient, a reservoir associated with the sensing module and containing a calibration fluid, and a conduit configured to deliver calibration fluid from the reservoir to the implant site.

Figure 1:
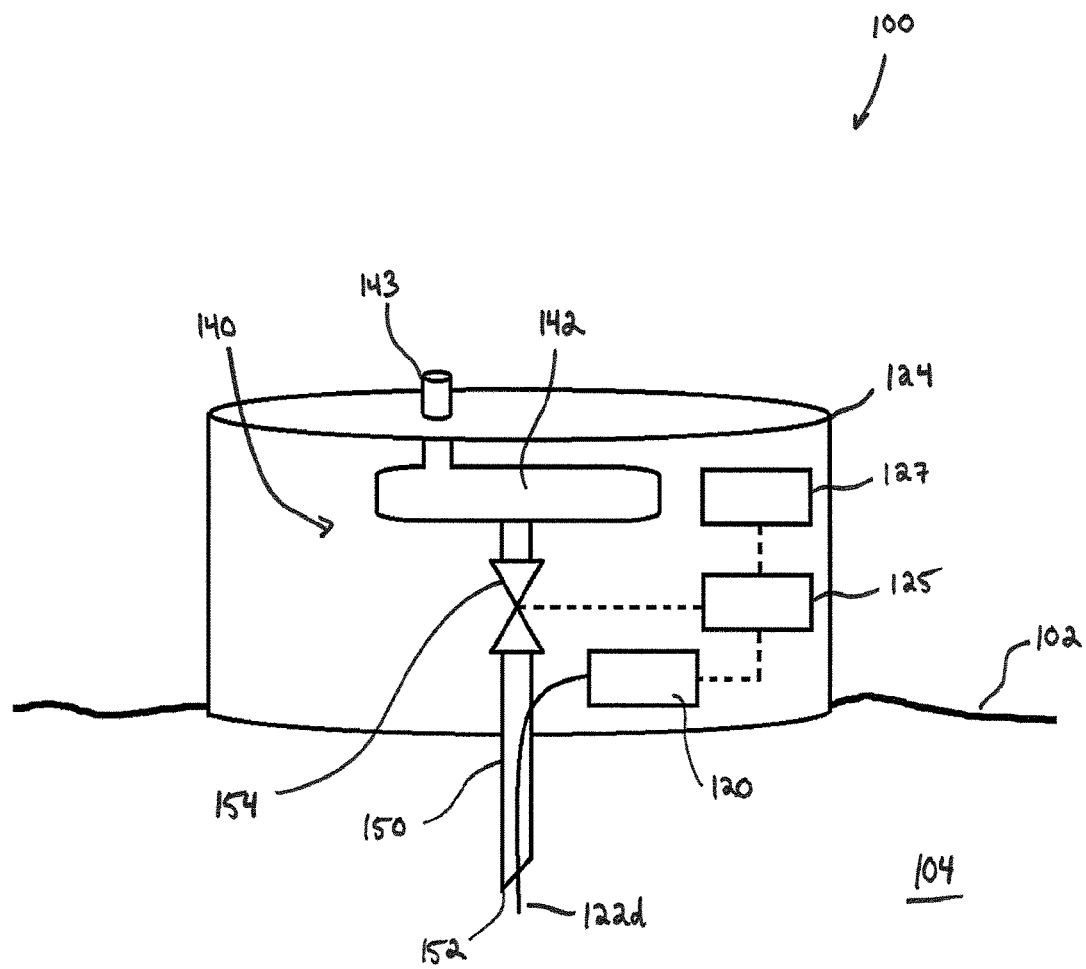
FIG. 1 is a schematic representation of an exemplary analyte monitoring system in accordance with various aspects of the present teachings.

With specific reference now to FIG. 1, one exemplary embodiment of an analyte monitoring system 100 is depicted in schematic diagram. As shown in FIG. 1, the analyte monitoring system 100 is disposed on a patient's skin 102 and includes a sensing module 120 having a sensor 122 implanted at an implant site within the patient. The depicted analyte monitoring system 100 additionally includes a calibration system 140 having a reservoir 142 for containing a calibration fluid and a conduit 150 defining a fluid pathway through which the calibration fluid can be delivered from the reservoir 142 to the implant site.

Sensing modules 120 for use in accord with the present teachings can have a variety of configurations, but generally include one or more sensors configured to be disposed at an implant site so as to detect a parameter of the implant site. Various continuous sensing modules are known in the art and, when modified in accordance with the teachings herein, can be used to provide, for example, an in situ calibrated determination of the concentration of an analyte of interest at an implant site.

By way of non-limiting example, various implantable sensing modules known in the art utilize electrochemical or optical sensors to determine the concentration of one or more analytes of interest. Exemplary analytes include glucose, lactate, creatinine, oxygen, alcohol, urea, electrolytes (e.g. potassium, calcium, magnesium, manganese, bicarbonate, and sodium) and drugs.

Electrochemical sensing modules, for example, can determine the concentration of an analyte by measuring the oxidation or reduction of an electroactive compound at a working electrode (i.e., sensor). By exposing a sample containing an analyte of interest to an enzyme that reacts with the analyte to generate electroactive products, an electrical signal can be generated at the sensor indicative of the concentration of the analyte. With specific reference to glucose monitors, for example, electrochemical sensors can utilize an enzyme (e.g., glucose oxidase, glucose dehydrogenase) that reacts with glucose near the sensing element to generate hydrogen, hydrogen peroxide, or other electroactive species oxidized or reduced at the working electrode to generate an electrical signal correlated to the concentration of glucose.

Optical sensors, on the other hand, can monitor an analyte of interest by detecting the interaction of electromagnetic radiation with the analyte directly or, for example, indirectly through the production or consumption of optically-detectable species following an enzymatic reaction of the analyte. By way of example, it is known that the concentration of clinically relevant analytes (e.g., glucose, alcohol, urea, creatinine, etc.) can be determined directly by analyzing NIR, IR or Raman spectra from body fluids (e.g., serum, blood, saliva, urine, ISF, etc.). Alternatively, as will be appreciated by a person skilled in the art, optical sensors can be based on the fact that the concentration of molecules such as $O_2$, $H_3O^+$, and $CO_2$ commonly produced or consumed by a chemical reaction of the analyte of interest can be detected using absorbing or fluorescing indicators that change their absorption or fluorescence based on the concentration of the above-referenced molecules. By way of example, pH indicators can be immobilized on a surface of a sensing module in contact with a biological fluid such that pH changes resulting from enzymatic reaction of the analyte of interest can be detected. Likewise, a variety of reagent phases have been used in optical oxygen sensors (e.g., pyrenebutyric acid or perylenebutyrate) and $NH_3$ sensors (e.g., ninhydrin). As will be appreciated by a person skilled in the art in light of the present teachings, these known optical sensing modalities can be modified to monitor clinically relevant parameters by immobilizing a suitable enzyme that interacts with the analyte of interest to change the concentration of the chemical parameter for which the optical measurement is sensitive (e.g., $O_2$, pH, $CO_2$, etc.).

U.S. Patent Pub. No. 2008/0027296 of Hadvary et al., which is incorporated by reference in its entirety, describes several exemplary sensing modules using electrochemical or optical sensors suitable for analyte monitoring devices that can be modified in accordance with the present teachings. As will be appreciated by a person skilled in the art, such electrochemical and optical sensing modules (and any other analyte sensing modalities known in the art) can be constructed in accordance with standard procedures for such sensors and modified in accordance with teachings herein.

With specific reference again to FIG. 1, the depicted exemplary sensing module 120 is contained within a sensor housing 124 and includes a sensor 122 extending therefrom. As will be appreciated by a person skilled in the art, the sensor 122 can be implanted in a patient at a variety of locations so as to be in contact with the biological fluid to be tested (e.g., interstitial fluid, intravascular fluid, urine, etc.). By way of example, the sensor housing 124 can be disposed on the skin surface 102 such that the sensor 122 extends to a depth below the skin surface 102. As shown, for example, the sensor 122 can extend from the skin surface into subcutaneous tissue 104 so as to be in contact with subcutaneous interstitial fluid. It should be appreciated that the sensor housing 124 can alternatively be positioned fully within tissue.

The sensor 122 can have a variety of configurations but is generally configured to sense one or more parameters when implanted at an implant site for an extended period of time (e.g., from about several hours to a few days). In various embodiments, the sensor 122 can be shaped, for example, to minimize trauma and/or pain experienced by the patient as the sensor 122 is inserted into the patient. By way of example, the sensor 122 can be a microneedle having a distal tip 122d configured to pierce the skin when the sensor housing 124 is pressed onto the skin surface 102.

As noted above, the sensor 122 can include one or more sensing sites on or about which a sensing signal is produced and/or enzymatic reactions occur. By way of example, the sensor 122 depicted in FIG. 1 can include one or more sensing sites disposed on or near the distal tip 122d upon which enzymes are immobilized so as to generate an electrochemical reaction at the sensing site. Likewise, the sensor 122 can be an optical sensor that can detect the analyte of interest directly or indirectly as discussed otherwise herein. By way of non-limiting example, exemplary sensors can aid in detecting the presence and/or quantity of one or more of glucose, lactate, creatinine, oxygen, alcohol, urea, electrolytes (e.g. potassium, calcium, magnesium, manganese, bicarbonate, and sodium) and drugs.

As will be appreciated by a person skilled in the art in light of the teachings herein, the sensor housing 124 can additionally contain a variety of other features. By way of non-limiting example, the sensor housing 124 can include a control and/or data processing module 125 operatively coupled to the sensing module 120 that can analyze, for example, electrochemical signals generated by the sensor 122 so as to calculate a concentration of the analyte of interest at the implant site. In some aspects, based on signals and/or data received, the same or different controller can control a calibration procedure, as discussed in detail below. Alternatively or additionally, a transmitter 127 (e.g., radio, Bluetooth®, etc.) can be contained within the housing for transmitting a raw signal generated by the sensor 122 and/or processed data to a remote receiver for further processing, storage, and/or display to the patient or caretaker. In some aspects, the sensor housing can additionally include one or more reservoirs and pumps configured to automatically deliver medication (e.g., insulin) to treat a patient's condition in response to the calculated concentration of the analyte. Additional exemplary analyte monitoring systems are discussed in detail in U.S. Patent Pub. No. 20090299276 of Brauker et al., U.S. Patent Pub. No. 20080027296 of Hadvary et al., U.S. Pat. No. 6,579,690, and U.S. Pat. No. 6,477,395 of Schulman et al., and U.S. Pat. No. 7,949,382 of Jina et al., all of which are incorporated by reference in their entireties.

As noted above, the depicted analyte monitoring system 100 additionally includes a calibration system that can enable in situ calibration of the sensing module 120. As shown in FIG. 1, the exemplary calibration system includes a reservoir 142 and a conduit 150 defining a fluid pathway through which a calibration fluid having a known concentration of the analyte of interest can be delivered from the reservoir 142 to the implant site. In some aspect, as will be discussed in detail below, the detected value of the analyte of interest at the implant site following delivery of the calibration fluid can be used to determine a calibration value and therefore a calibration-corrected value for the measurement of the analyte of interest.

Reservoirs in accordance with the present teachings can have a variety of configurations but are generally configured to contain one or more reagents effective to calibrate the sensor. By way of example, the reservoir 142 can contain a calibration fluid having a known concentration of the one or more analytes to be sensed by the sensing module 120. As discussed otherwise herein, the calibration fluid can contain known concentrations of one or more of the following analytes: glucose, lactate, creatinine, oxygen, alcohol, urea, electrolytes (e.g. potassium, calcium, magnesium, manganese, bicarbonate, and sodium), and drugs, all by way of non-limiting example.

As will be discussed in detail below, the reservoir 142 can be configured to contain a sufficient volume of calibration reagents such that a pre-determined amount of calibration fluid can be delivered to the implant site one or more times throughout the period of implantation of the sensor. Alternatively or additionally, the reservoir 142 can include a portal 143 through which calibration reagent can be added thereto, for example, to refill the reservoir 142. In various aspects, the reservoir can have a volumetric capacity of less than about 10 mL. For example, the reservoir can hold from about 0.5 to about 10 mL of calibration fluid, from about 0.5 to about 5 mL, from about 5 to about 10 mL, or from about 1 to about 5 mL.

As shown in FIG. 1, the conduit 150 can be fluidly coupled to the reservoir 142 and define a fluid flow pathway that allows calibration fluid, for example, to be transported from the reservoir 142 to the outlet 152 of the conduit 150 so as to deliver the calibration fluid to the implant site. The conduit 150 can have a variety of configurations and can be made of a variety of materials, but is generally configured such that its outlet 152 is proximate to the implant site so as to deliver fluid from the reservoir 142 thereto, as discussed otherwise herein. In the exemplary embodiment depicted in FIG. 1, for example, the conduit 150 can be a cannula or sheath (rigid, non-rigid, or flexible), for example, that extends from the reservoir 142 and includes a central lumen through which fluid from the reservoir 142 can flow and/or be pumped.

Though the conduit 150 and the sensor 122 can have a variety of orientations, the conduit 150 and the sensor 122 are generally positioned relative to one another such that fluid delivered by the conduit 150 to the implant site can be sensed by the sensor 122. As shown in FIG. 1, for example, the conduit 150 and the sensor 122 can be coupled such that a portion of the sensor 122 extends through the conduit 150. That is, the conduit 150 can enclose at least a portion of the distal end of the sensor 122 such that fluid is delivered to the implant site in the fluid pathway between the conduit 150 and the sensor 122. Additionally, in some aspects, the outlet 152 can be disposed relative to the sensor 122 to remove contaminants (e.g., proteins, microclots) disposed on the surface of the sensor 122 that could interfere with the accuracy of the analyte measurements.

As will be appreciated by a person skilled in the art, various mechanisms can be used to control the fluid flowing from the reservoir 142 and delivered by the conduit 150 to the implant site. As will discussed in detail below, a controller (not shown) can be associated with the calibration system for controlling, for example, a pump (e.g., piston, peristaltic, piezoelectric, or otherwise) and/or valve 154 associated with the calibration system so as to control the delivery of calibration fluid to the implant site. By way of example, the pump and/or valve 154 can be operatively coupled to the control and/or data processing module 125 that can control the volume delivered, volumetric flow rate, fluid flow pressure, and frequency and timing of the delivery of calibration flow, etc. By way of non-limiting example, the number of repetitions of calibration fluid delivery can be 1 to 5, the amount of the calibration fluid delivered can be from about 2 to about 50 microliters for each delivery, and the time interval between each delivery or groups of delivery can be from about 1 minute to about 24 hours. Alternatively, the fluid can be delivered manually, for example, by depressing an actuator (e.g., piston) configured to transport fluid from the reservoir 142 and through the conduit 150 to the implant site.

Figure 2:
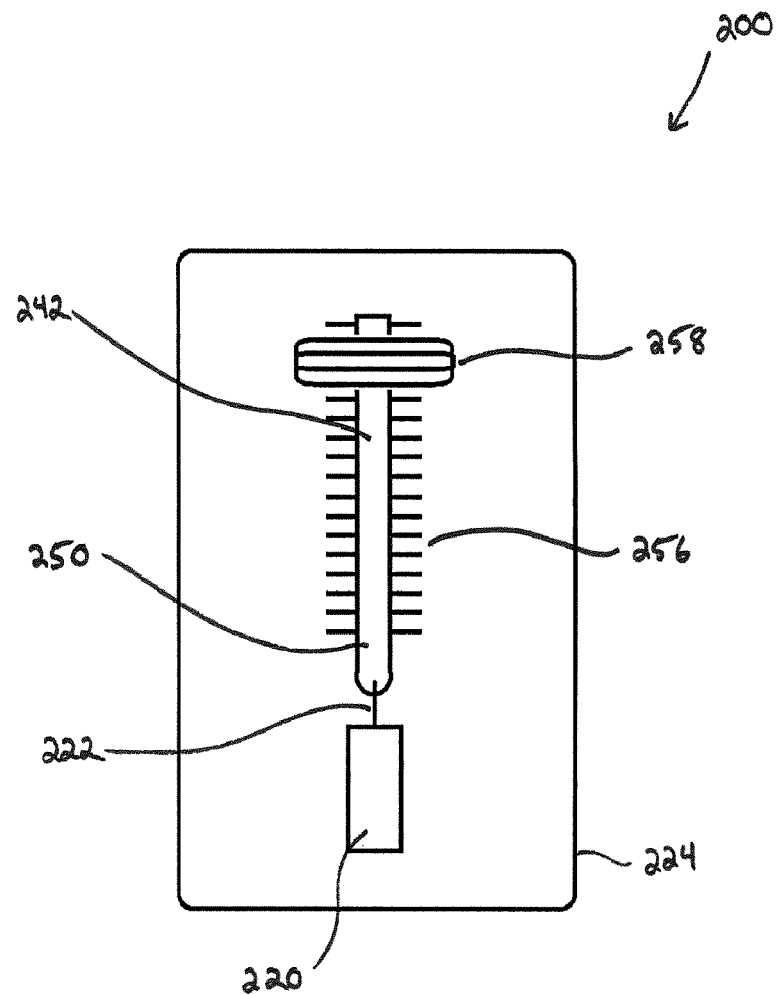
FIG. 2 is a top view schematic representation of another exemplary embodiment of an analyte concentration monitoring system in accordance with various aspects of the present teachings.

With reference now to FIG. 2, another exemplary embodiment of an analyte monitoring system 200 is depicted in schematic diagram. The analyte monitoring system 200 can be substantially similar to that depicted in FIG. 1, but FIG. 2 depicts additional detail regarding an exemplary embodiment of a pump for pumping calibration fluid to an implant site. As above, the analyte monitoring system 200 includes a sensor housing 224 configured to be disposed on a patient's skin. The sensor housing 224 can additionally contain a sensing module 220 having a sensor 222 extending therefrom for implantation at an implant site and a reservoir 242 for containing a calibration fluid having a known concentration of an analyte of interest. As above, the sensor 222 can extend through the fluid flow pathway defined by the conduit 250 between the reservoir 242 and the implant site.

As noted above, various mechanisms can be used to control the fluid flowing from the reservoir and delivered by the conduit to the implant site. As shown in the embodiment depicted in FIG. for example, the pump can comprise a track 256 having discrete steps formed therealong. A roller 258 is configured to engage each of the discrete steps as it moves along the track (e.g., top to bottom as seen in FIG. 2). The reservoir 242, which can be formed by a flexible material, can be compressed as the roller 258 moves between discrete steps, thereby expelling a volume of calibration fluid from the reservoir 242 into the conduit 250 for delivery to the implant site. As will be appreciated by a person skilled in the art, the reservoir 242 and discrete steps can be dimensioned such that a predetermined amount of calibration fluid is pumped from the reservoir for each of the discrete steps that the roller 258 advances. It will also be appreciated that the roller 258 can be actuated manually or automatically.

Similarly, in another exemplary embodiment, the reservoir 242 can be semi-circular. In such an embodiment, the roller 258 could rotate, like the hands of clock, to compress a portion of the reservoir. As above, each actuation could expel a predetermined volume of calibration fluid from the reservoir.

Figure 3:
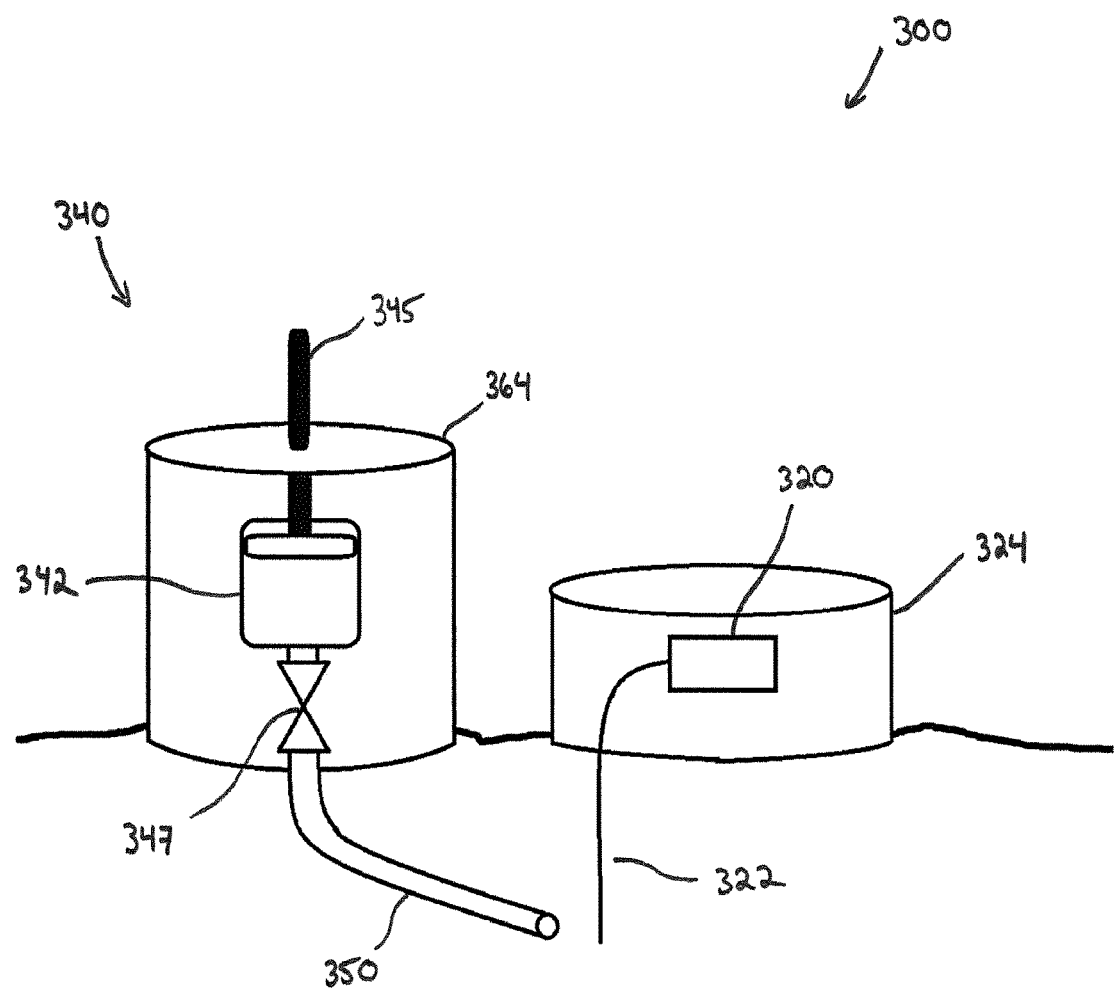
FIG. 3 is a schematic representation of another embodiment of another exemplary analyte monitoring system in accordance with various aspects of the present teachings.

With reference now to FIG. 3, another exemplary embodiment of an analyte monitoring system 300 is depicted in schematic diagram. The system 300 can include a sensor housing 324, a sensor module 320, and an implantable sensor tip 322 (e.g., a microneedle). The analyte monitoring system 300 can be similar to that depicted in FIG. 1, but differs in that the calibration system 340 is not substantially contained within the sensor housing 324. Rather, the calibration system 340 comprises a separate calibration housing 364 containing a reservoir 342 of calibration fluid.

Moreover, as discussed above with reference to FIG. 1, the conduit and sensor can have a variety of orientations, but are generally positioned relative to one another such that fluid delivered by the conduit to the implant site can be sensed by sensing elements on the sensor. As shown in FIG. 3, for example, rather than surrounding a distal end of the sensor 322, the conduit 350 extends through the patient's tissue at a position adjacent the sensor 322. Moreover, in various aspects, the outlet 352 of the conduit 350 can be oriented relative to the sensor 322 such that calibration fluid delivered to the implant site impinges on the sensor 322 (and particularly the sensing sites formed thereon). In such a manner, the fluid delivered by the conduit may be effective to not only allow for calibration, as discussed in detail below, but additionally act to remove contaminants disposed on the surface of the sensing sites that may be interfering with the accuracy of the analyte measurements. Calibration fluid can be dispensed from the reservoir 342 via a pump (e.g., piston 345). Alternatively, fluid in the reservoir 342 can be pre-pressurized, for example, and released by periodic or otherwise scheduled or controlled opening and closing of a microvalve 347.

In light of the above teachings, methods for calibrating the sensing modules will now be discussed in further detail with reference to FIG. 4, which provides an exemplary depiction of the sensed concentration of the analyte at the implant site following the delivery of a predetermined amount of a calibration fluid having a known concentration of an analyte of interest. The calibration methods can be implemented, for example, via a control and/or data processing module 125, as described above in connection with FIG. 1. Though reference is made to the concentration of glucose, a person skilled in the art will appreciate the methods, systems, and devices described herein can be applied to additional and/or alternative analytes as otherwise discussed herein. It will further be appreciated by a person skilled in the art, that though the depicted concentration of glucose level could be determined based on an electrical signal (e.g., current) generated by a sensor in contact with interstitial fluid at the implant site, the concentration of glucose in the blood could be measured directly or derived based on an estimated relationship of glucose levels between the various compartments. By way of non-limiting example, it has been estimated that the concentration of glucose in subcutaneous interstitial fluid can be generally about 15% lower than that of the blood.

Figure 4:
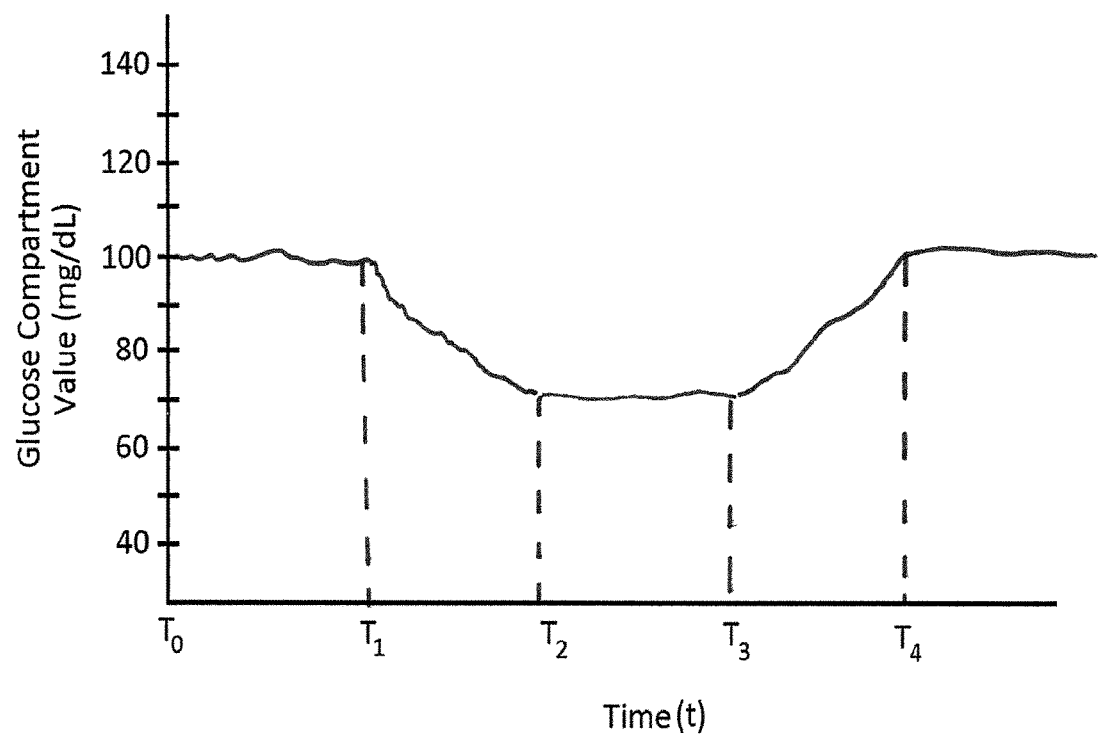
FIG. 4 is an exemplary graphical depiction of the concentration of an analyte at the implant site as sensed by an exemplary analyte monitoring system in accordance with various aspects of the present teachings.

As shown in FIG. 4, the concentration of glucose within the interstitial fluid between time $T_0$ and $T_1$ remains substantially steady at about 100 mg/dL. At time $T_1$, a calibration procedure can be initiated, for example, by delivering to the implant site a predetermined amount of an exemplary calibration solution having a known concentration of glucose (e.g., 60 mg/dL). Given that the concentration of the exemplary calibration fluid is lower than the steady state concentration in the patient's interstitial fluid, the sensed concentration of glucose at the implant site can decline between time $T_1$ and $T_2$ until a minimum concentration is reached. For purposes of discussion, $(T_2-T_1)$ represents the equilibration time. After reaching the minimum concentration, the concentration of glucose increases between time $T_3$ and $T_4$ as the interstitial fluid at the implant site returns to equilibrium with the surrounding interstitial fluid. After reaching equilibrium, the concentration of glucose can return, for example, to a steady state concentration at about 100 mg/dL (i.e., for $t>T_4$). A person skilled in the art will appreciate that a concentration of the calibration fluid can alternatively be higher (e.g., 160 mg/dL) than a typical steady state concentration of glucose in the interstitial fluid such that the concentration of glucose at the implant site will instead increase following delivery of the calibration fluid.

As will be appreciated by a person skilled in the art in light of the teachings herein, by analyzing the sensor signals before, during, and/or after delivery to the implant site of a predetermined amount of calibration fluid having a known concentration of analyte, a calibration value can be calculated based on the differences, for example, between values determined by the sensors as depicted in FIG. 4 and a theoretical, expected curve. Exemplary factors in the determination of the calibration value include the difference between the expected minimum concentration of glucose and the minimum detected value, the equilibration time, the time to return to the steady state value following delivery, and/or the rate of change of the sensed values during the time intervals $T_1<t<T_2$ and $T_3<t<T_4$. After determining the calibration value, the measured value of glucose, for example, can be adjusted in light of the calibration value to provide a calibration-corrected value. By way of example, the measured values as provided by the sensor(s) at $t<T_1$ (i.e., at equilibrium and/or prior to delivery of the calibration fluid) and/or $t>T_4$ (i.e., at equilibrium and/or subsequent to delivery of the calibration fluid) can be adjusted in light of the determined calibration value.

Figure 5:
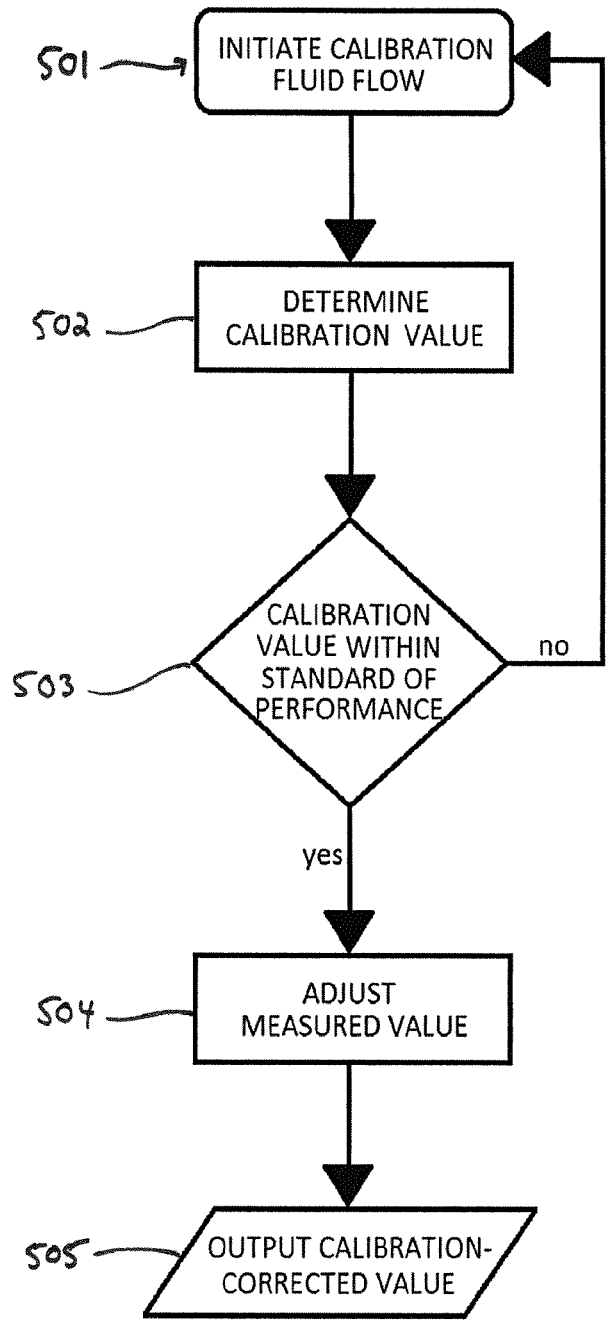
FIG. 5 is a flow chart depicting an exemplary calibration procedure in accordance with various aspects of the present teachings.

Accordingly, the systems, device, and methods described herein can enable the in situ calibration of a sensor implanted in a patient without requiring additional extraction of a sample from a patient. With reference now to FIG. 5, an exemplary calibration procedure can be initiated by delivering the calibration solution of a known concentration of the analyte from a reservoir to the implant site of the sensor (e.g., step 501). As a result, the sensor signal can change, reflecting a change in the concentration of the analyte at the implant site. As discussed above, the change in the sensor's signal can then be used to determine a calibration value, for example, via a control and/or data processing module (e.g., step 502). By way of example, the calibration value can be calculated by dividing a measured concentration of glucose (e.g., the minimum concentration of glucose at time $T_2$) with the known concentration of the calibration solution. As shown at step 503, in various aspects, if the calibration value and/or measured concentration deviates more than expected or is otherwise outside of the standard of performance (e.g., within the range of about +/−1%, about +/−5%, or about +/−10% of the known concentration of the calibration fluid), additional calibration fluid can be delivered to the implant site, the minimum concentration can be measured, and the calibration value recalculated until the calibration value or measured concentration is equal to or approximately within the standard of performance of the expected concentration. Subsequently, as depicted at step 504, the sensor can be recalibrated and/or the measured values (i.e., the concentration in the absence of calibration fluid) can be adjusted to a calibration-corrected value based, for example, on the most recent calibration value or an average of the previously-determined calibration values, and/or in accordance with calibration algorithms, known in the art or hereafter developed and modified in accordance with the teachings herein. As depicted in step 505, the calibration-corrected value can be displayed to a patient and/or caretaker.

In various aspects, the methods and systems described herein can allow for the substantially continuous monitoring of analyte concentration levels in a biological fluid. By way of example, in some aspects, the calibration procedures (e.g., delivery of calibration fluid to the implant site) can be repeated at various times during the period of time during which the sensor is implanted. It should be appreciated that calibration procedures in accordance with the present teachings can be automated to occur at a predetermined time interval or preset, for example, by a manufacturer. Further, if a calibration value appears abnormal, a controller for processing the sensor data and calibration information can control an additional calibration procedure to be initiated. Alternatively or in addition, a user or caretaker can initiate the calibration procedure. Moreover, as discussed above, the calibration procedure can be repeated to help maintain the sensing sites free from contaminants. By way of example, the calibration fluid can be delivered to the sensor so as to clean a surface thereof. By way of non-limiting example, the calibration procedure can be configured to occur at least once per day, at least four times per day, at least once per hour, or at least once per minute. Moreover, during each calibration procedure, about 2 to about 50 microliters of calibration fluid can be delivered to the implant site. In addition, the calibration procedure can be repeated such that, for example, one to ten calibration procedures are repeated immediately one after the other. If the sensor appears calibrated (e.g., the calibration values are similar within a standard of performance), the calibration procedure can be delayed for the predetermined time interval.

One skilled in the art will appreciate further features and advantages of the presently disclosed methods, systems and devices based on the above-described embodiments. Accordingly, the presently disclosed methods, systems and devices are not to be limited by what has been particularly shown and described, except as indicated by the appended claims. All publications and references cited herein are expressly incorporated herein by reference in their entirety.

What is claimed is:

1. A system for monitoring the concentration of an analyte, comprising:
   a housing configured to be disposed on a patient's skin surface, the housing comprising:
      a reservoir configured to hold a glucose calibration fluid, the glucose calibration fluid having a known concentration of glucose included therein, the reservoir being in fluid connection with a conduit through which the glucose calibration fluid is delivered from the reservoir to an implant site positioned at a depth under the patient's skin surface; and
      a sensor assembly comprising a glucose sensor, the glucose sensor being configured to extend from the housing to the implant site when the housing is disposed on the patient's skin surface, said glucose sensor being configured to obtain measurements of concentration level of glucose present in a subcutaneous interstitial fluid at the implant site at a plurality of points in time before and after delivery of the calibration fluid to the implant site; and
      a calibration system configured to calibrate the glucose sensor in situ using the measurements of the concentration level of glucose in the subcutaneous interstitial fluid following delivery of the glucose calibration fluid to the implant site.

2. The system of claim 1, wherein the glucose sensor comprises a microneedle configured to pierce the skin.

3. The system of claim 1, wherein the glucose sensor extends through a fluid pathway defined by said conduit.

4. The system of claim 3, wherein the conduit comprises a sheath enclosing a distal end of the glucose sensor and wherein the glucose calibration fluid is delivered to the implant site through the fluid pathway between the sheath and the sensor.

5. The system of claim 1, wherein the housing comprises a transmitting unit.

6. The system of claim 1, wherein the housing further comprises a pump configured to pump said glucose calibration fluid through said conduit.

7. The system of claim 6, further comprising a controller configured to control the pump to deliver a predetermined amount of the glucose calibration fluid to the implant site.

8. The system of claim 7, wherein the controller is configured to control the pump to deliver the predetermined amount of the glucose calibration fluid to the implant site a predetermined number of times with a predetermined time interval.

9. The system of claim 7, wherein the controller controls a number of repetitions of glucose calibration fluid delivery, an amount of the glucose calibration fluid delivered, and a time interval between each delivery.

10. The system of claim 9, wherein the controller is configured to control the number of repetitions of the delivery of the glucose calibration fluid to be in a range of 1 to 5, to control the amount of the glucose calibration fluid delivered to be in a range of from about 2 to about 50 microliters for each delivery, and to control the time interval between each delivery to be in a range of from about 1 minute to about 24 hours.

11. The system of claim 1, wherein said glucose sensor comprises one of an electrochemical sensor and an optical sensor.

12. The system of claim 1, wherein the glucose sensor comprises one or more sensing sites.

13. The system of claim 12, wherein an outlet of the conduit is disposed relative to the one or more sensing sites such that the glucose calibration fluid delivered by the conduit to the implant site is directed at the one or more sensing sites.

14. The system of claim 13, wherein an outlet of the conduit is further configured such that the glucose calibration fluid delivered to the implant site also removes contaminants from the sensor.

* * * * *

UNITED STATES PATENT AND TRADEMARK OFFICE
CERTIFICATE OF CORRECTION

PATENT NO. : 10,010,274 B2
APPLICATION NO. : 14/365172
DATED : July 3, 2018
INVENTOR(S) : James Winkelman Page 1 of 1

It is certified that error appears in the above-identified patent and that said Letters Patent is hereby corrected as shown below:

On the Title Page

Item (71) Applicant and (72) Inventor's address should read:
Chestnut Hill, MA

Signed and Sealed this
Sixth Day of November, 2018

Andrei Iancu
*Director of the United States Patent and Trademark Office*